(12) United States Patent
Belkacem

(10) Patent No.: US 11,033,214 B1
(45) Date of Patent: Jun. 15, 2021

(54) WEARABLE EYE TRACKING SYSTEM

(71) Applicant: United Arab Emirates University, Al Ain (AE)

(72) Inventor: Abdelkader Nasreddine Belkacem, Al Ain (AE)

(73) Assignee: UNITED ARAB EMIRATES UNIVERSITY, Alain (AE)

( * ) Notice: Subject to any disclaimer, the term of this patent is extended or adjusted under 35 U.S.C. 154(b) by 0 days.

(21) Appl. No.: 16/877,858

(22) Filed: May 19, 2020

(51) Int. Cl.
| | |
|---|---|
| A61B 5/375 | (2021.01) |
| A61B 5/00 | (2006.01) |
| A61B 5/16 | (2006.01) |
| A61B 5/18 | (2006.01) |
| G16H 10/20 | (2018.01) |
| G06N 7/02 | (2006.01) |
| A61B 5/291 | (2021.01) |
| A61B 5/316 | (2021.01) |
| A61B 5/389 | (2021.01) |
| A61B 5/398 | (2021.01) |

(52) U.S. Cl.
CPC ............. *A61B 5/163* (2017.08); *A61B 5/18* (2013.01); *A61B 5/291* (2021.01); *A61B 5/316* (2021.01); *A61B 5/389* (2021.01); *A61B 5/398* (2021.01); *A61B 5/6815* (2013.01); *A61B 5/7264* (2013.01); *G06N 7/02* (2013.01); *G16H 10/20* (2018.01); *A61B 2562/0215* (2017.08)

(58) Field of Classification Search
None
See application file for complete search history.

(56) References Cited

U.S. PATENT DOCUMENTS

| 10,235,859 B1 * | 3/2019 | Hiles ............... B60K 28/066 |
| 2003/0013981 A1 * | 1/2003 | Gevins ............... A61B 5/16 |
| | | 600/544 |

(Continued)

FOREIGN PATENT DOCUMENTS

WO   WO-2017125082 A1 *  7/2017  .......... A61B 5/0478

OTHER PUBLICATIONS

Adbelkader Nasreddine Belkacem, "Real-Time Control of a Video Game Using Eye Movements and Two Temporal EEG Sensors", Article, Jul. 2015, 1-10, Computational Intelligence and Neuroscience, Hindawi.

(Continued)

*Primary Examiner* — Etsub D Berhanu
(74) *Attorney, Agent, or Firm* — Hayes Soloway P.C.

(57) ABSTRACT

There is provided a method and wearable eye-tracking device for determining a fatigue level of a user, the method comprising the steps of acquiring two channels of an observed EEG (electro-encephalogram) signal using a plurality of silver chloride (AgCl) electrodes positioned in contact with and around the user's ear, obtaining user's inputs for a plurality of psychological questions and calculating an evaluation metric, decomposing the observed EEG signal using filter and blind signal separation techniques into a plurality of features, classifying and converting the plurality of features in combination with the calculated evaluation metric to a fatigue level using a classification algorithm and fuzzy logic and outputting the obtained fatigue level along with customized prompts to the user through visual and audio signals for preventing an accident.

19 Claims, 4 Drawing Sheets

(56) References Cited

U.S. PATENT DOCUMENTS

| | | | | |
|---|---|---|---|---|
| 2003/0167019 A1* | 9/2003 | Viertio-Oja | ........... | A61B 5/4821 600/544 |
| 2004/0044293 A1* | 3/2004 | Burton | ...................... | B60L 3/02 600/544 |
| 2004/0073098 A1* | 4/2004 | Geva | ................ | A61M 16/0051 600/300 |
| 2005/0010116 A1* | 1/2005 | Korhonen | ............ | A61B 5/4035 600/481 |
| 2009/0024044 A1* | 1/2009 | Virtanen | .............. | A61B 5/6814 600/509 |
| 2010/0010289 A1* | 1/2010 | Clare | ....................... | A61B 5/16 600/27 |
| 2010/0036290 A1* | 2/2010 | Noguchi | ................. | A61B 5/165 600/595 |
| 2011/0301487 A1* | 12/2011 | Abeyratne | ............. | A61B 5/048 600/544 |
| 2013/0137764 A1* | 5/2013 | Ahnaou | ................... | A61P 25/26 514/489 |
| 2013/0184603 A1* | 7/2013 | Rothman | ............. | A61B 5/0476 600/544 |
| 2014/0240132 A1* | 8/2014 | Bychkov | .................. | A61B 5/18 340/576 |
| 2016/0090097 A1* | 3/2016 | Grube | ...................... | A61B 5/18 340/576 |
| 2016/0119726 A1* | 4/2016 | Pontoppidan | ........... | G06F 3/015 600/25 |
| 2016/0278651 A1* | 9/2016 | Lu | ......................... | A61B 5/0492 |
| 2017/0039045 A1* | 2/2017 | Abrahami | ............. | A61B 5/1118 |
| 2018/0116514 A1* | 5/2018 | Turner | ................. | A61B 5/7203 |
| 2018/0186234 A1* | 7/2018 | Mestha | ................. | B60W 50/14 |
| 2019/0223747 A1* | 7/2019 | Chou | ................... | A61B 5/0478 |

OTHER PUBLICATIONS

Adbelkader Nasreddine Belkacem, "Online Classification Algorithm for Eye-Movement-Based Communication Systems Using Two Temporal EEG Sensors", Journal, 2015, 40-47, vol. 16, Biomedical Signal Processing and Control, Science Direct.

Adbelkader Nasreddine Belkacem, "Classification of Four Eye Directions from EEG Signals for Eye-Movement-Based Communication Systems", Article, Dec. 2014, 581-588, vol. 34, No. 6, Journal of Medical and Biological Engineering.

* cited by examiner

WEARABLE EYE TRACKING SYSTEM

FIELD OF THE INVENTION

The present invention relates to an eye tracking system, and more particularly a wearable eye tracking system for detecting a health condition of a user particularly signs of fatigue and drowsiness.

BACKGROUND OF THE INVENTION

Background description includes information that may be useful in understanding the present invention. It is not an admission that any of the information provided herein is prior art or relevant to the presently claimed invention, or that any publication specifically or implicitly referenced is prior art.

Eye tracking is a sensor technology which makes it possible for a computer or any other device to detect and perceive where a person is looking. An eye tracker can detect the presence, attention and focus of a user and allows for obtaining insights into human behavior. Portable eye tracking devices have been previously described and are available for commercial purchase such as TOBII and Google glasses. However, existing portable eye tracking systems are inconvenient and suffer performance degradation when the equipment moves relative to the user's head. For example, glasses may slip relative to a user's nose, requiring the user to manually adjust glasses as they are worn. This hinders smooth functioning of the user and obstructs the user's field of vision. Also, for designs requiring calibration, such movement of the glasses relative to the wearer's head result in negating the calibration and significantly degrade the accuracy of the readings.

Another already known method for recording eye movements and blinking patterns involves Electro-oculography (EOG), a technique that enables detection of eye movements. This technique works on the basis that the eye may be modeled as a dipole, with the cornea and the retina being positive and negative potentials, respectively. With the movement of the eyeball, an electric field is generated, which is then be measured. A number of human-machine interfaces (HMIs) have been based on EOG signals (using biosensors or EOG electrodes) to detect and classify eye movements, considering that EOG is a simple and easy method to measure eye movement. However, EOG would be inconvenient for applications, such as driving, since this reduces the field of vision. Other drawbacks include discomforts associated with electrodes positioned around the eyes and poor esthetics. Variations resulting from facial muscles can also affect quality of the EOG signals.

There are various driver monitoring systems also available for commercial purchase (a vehicle safety system introduced by Toyota), wherein infrared sensors or CCD cameras are utilized for monitoring the driver's actions when driving. Such safety systems were later on installed and implemented in various other vehicle manufacturing companies. Similar mobile applications in the market include the SomnoAlert and Anti Sleep Pilot Drowsy Driving application. Another product serving this purpose is the U-Wake wearable brainwave sensor, which is a unit resting on a driver's forehead like a headband, measuring the brain's electrical pulses. However this device is obstructive and inconvenient to a user considering that this needs to be worn on the user's forehead, and there are high chances of this device slipping off—during operation, which will rather prove rather disastrous to the user. Hence, the problem of obstructing field of vision of the driver persists.

Other similar products or systems for driver safety include using the cell phone cameras or other embedded cameras for monitoring the user, however such cameras are sensitive to light, expensive, and further requires the user to always keep eyes open and within the vision field of the camera. Hence, such devices are not practical in real-life applications and the image processing takes up too much memory.

In light of these problems, electroencephalography (EEG) may offer advantages to EOG if employed within an eye tracking device, the biggest challenges being reducing the number of sensors used and extracting appropriate features of eye movements from the EEG signal. Accordingly, there exists a need for an eye tracking system or device design, which is compact and in no way will obstruct field of vision of a user.

SUMMARY OF THE INVENTION

Therefore it is an object of the present invention to develop a compact eye tracking device for detecting signs of fatigue and drowsiness in a user.

The present invention involves a method of determining a condition of a user using an eye-tracking device, the method comprising the steps of obtaining two channels of an observed EEG (electro-encephalogram) signal using a plurality of silver chloride (AgCl) electrodes positioned in contact with the user's ear; and processing the two channels to determine the condition of the user.

In an embodiment of the present invention, processing the two channels comprises obtaining user's inputs for a plurality of psychological questions and calculating an evaluation metric, decomposing the observed EEG signal using filter and blind signal separation techniques into a plurality of features, classifying and converting the plurality of features in combination with the calculated evaluation metric to a condition of the user using a classification algorithm and fuzzy logic classifier and outputting the obtained condition along with customized prompts to the user through visual and audio signals for preventing an accident.

In another embodiment of the present invention, the condition of the user is a fatigue level, a drowsiness level, or a physiological status.

In another embodiment of the present invention, the two channels of the observed EEG signal comprise two channels of eye movements or left and right electro-oculography (EOG) signals.

In another embodiment of the present invention, the observed EEG signal is decomposed into features comprising alpha and beta frequency bands, slow eye movements, blinking amplitudes and patterns and electromyography (EMG) amplitudes.

In another embodiment of the present invention, the plurality of psychological questions are customized based on a profile of the user, thereby enabling customized prompts to be provided to the user depending on the determined condition of the user.

In another embodiment of the present invention, the profile of the user is a professional driver, laborer or student.

In another embodiment of the present invention, the customized prompts are provided to the user through an LED indicator, a speaker component or a vibrator on the eye-tracking device.

In another embodiment of the present invention, the features obtained from decomposing the observed EEG signal are classified into patterns for deep learning using the classification algorithm, which is subsequently combined with the calculated evaluation metric as input to the fussy logic classifier.

In another embodiment of the present invention, an output of the fussy logic classifier is a percentage of the user's fatigue level.

In another embodiment of the present invention, the eye-tracking device is linked via BLUETOOTH with a mobile application installed on an electronic device or wireless device.

In another embodiment of the present invention, processing of the observed EEG signal is done using the mobile application.

As another aspect of the present invention, a wearable eye-tracking device is disclosed for determining a condition of a user, the eye-tracking device comprising two electrodes positioned in contact with the user's ear for obtaining an EEG (electro-encephalogram) signal from the user, where the electrodes are in electrical communication with a microprocessor for processing the EEG signal for determining the condition of the user.

In an embodiment of the present invention, the microprocessor is part of the wearable eye-tracking device; and a communication unit is in electrical communication with the microprocessor for sending a notification signal based on the determined user condition.

In another embodiment of the present invention, obtaining an EEG signal comprises observing the EEG signal using the electrodes and obtaining two channels of the observed EEG signal, and wherein processing the EEG signal comprises processing the two channels, the two channels of the observed EEG signal comprising two channels of eye movements or left and right electro-oculography (EOG) signals.

In another embodiment of the present invention, the processing the two channels comprises obtaining user's inputs for a plurality of psychological questions and calculating an evaluation metric, decomposing the observed EEG signal using filter and blind signal separation techniques into a plurality of features; and classifying and converting the plurality of features in combination with the calculated evaluation metric to a condition of the user using a classification algorithm and a fuzzy logic classifier; wherein, the notification signal comprises the determined status and customized prompts.

In another embodiment of the present invention, the communication unit comprises at least one of a LED indicator, a speaker and a vibrator.

In another embodiment of the present invention, the two electrodes are AgCl electrodes.

In another embodiment of the present invention, the device is adapted to be worn by the user such that it is positioned around the user's ear away from a visual field of the user, and wherein the device further comprises a support means for enabling the device to be fixed around the user's ear during operation.

In another embodiment of the present invention, the processing of the EEG signal comprises decomposing the EEG signal into features comprising alpha and beta frequency bands, slow eye movements, blinking amplitudes and patterns and electromyography (EMG) amplitudes.

In another embodiment of the present invention, the microprocessor is part of a mobile device in remote communication with the electrodes.

BRIEF DESCRIPTION OF THE DRAWINGS

The subject matter that is regarded as the invention is particularly pointed out and distinctly claimed in the claims at the conclusion of the specification. The foregoing and other aspects, features, and advantages of the invention are apparent from the following detailed description taken in conjunction with the accompanying drawings in which:

DETAILED DESCRIPTION OF THE INVENTION

The aspects of the device or system for tracking eye movements device and thereby detecting signs of fatigue and drowsiness in a user, according to the present invention will be described in conjunction with FIGS. 1-4. In the Detailed Description, reference is made to the accompanying figures, which form a part hereof, and in which is shown by way of illustration specific embodiments in which the invention may be practiced. It is to be understood that other embodiments may be utilized and logical changes may be made without departing from the scope of the present invention. The following detailed description, therefore, is not to be taken in a limiting sense, and the scope of the present invention is defined by the appended claims.

The proposed solution aims at designing a device for recording brain activity and thereby tracking various movements of a user's eyes. This primarily involves obtaining electrical signals using a compact radio device worn around the user's ears, which may additionally be used to detect frequency of blinking, yawning and direction of view of the user. Detection of these electrical signals leads to monitoring user or driver alertness, the degree of tiredness and exhaustion associated with the user or driver (along with other features such as the duration of travel, number of hours the user previously obtained sleep, and whether the user is driving at night or during the day). Upon detection by the device that the user is tired or drowsy, alerts are sent to a mobile application installed on an electronic device or wireless device, such as tips for the user to increase his attentiveness or vigilance.

The electronic device includes, but is not limited to a smart phone, a mobile phone, a personal digital assistant (PDA), an e-book reader, a notebook computer, GPS receivers and other devices that include appropriate hardware and software components for processing information. Wireless device in general includes but is not limited to, wireless cell phones, computers with wireless WAN connections, computers with wireless LAN connections, or other electronic devices capable of connecting to wireless networks.

In an embodiment of the present inevntion, the alerts or tips sent to the mobile application include instructions to stop the vehicle, wash face, have a coffee or to take a power nap. Further, at any point of operation of the eye tracking device, the user is able to view his or her alertness level through the mobile application (in percentage form e.g., 10% or 98% alertness).

EEG recording is an advantageous alternative to measure eye movements, considering that EEG signals include EOG artifacts, and is appropriate for use in applications such as driving safety systems because the sensors used do not reduce the field of vision. Another advantage of this method is the inclusion of established positions for EEG sensors around the user's ears.

Figure 1:
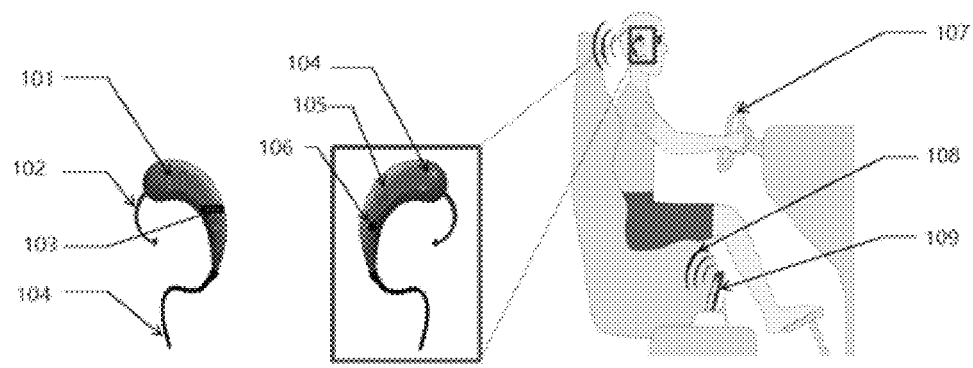
FIG. 1 illustrates a basic design of the eye tracking device, in accordance with the present invention.
Figure 2:
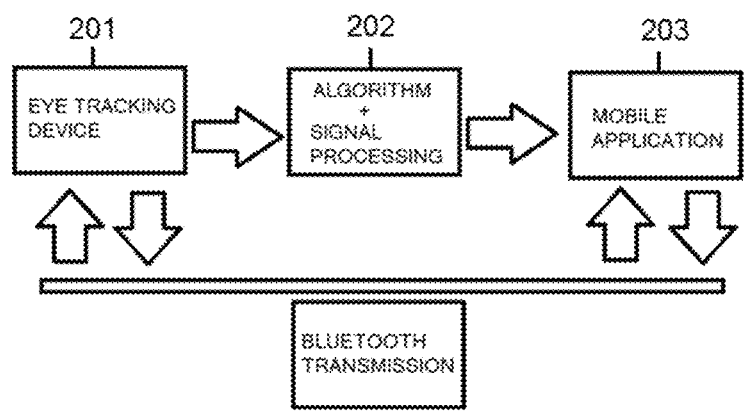
FIG. 2 depicts a flow chart of the eye tracking system, in accordance with the present invention.

FIG. 1 illustrates a design of the proposed eye-tracking device to record EOG and EEG signals. The device is designed such that the electrodes 101 are positioned around the user's ears, as this position is most suitable for distinguishing between four cardinal eye directions (or cardinal positions of gaze) of the user, namely upwards, downwards, right and left directions (which are divided into horizontal and vertical gaze).

The proposed eye-tracking device further includes a support 102 for holding the device on the user's ears, a USB or battery slot 103 with ground terminal, GND 104. Also included is a tri-colored LED indicator 104, a speaker 105 and a power button 106. In an embodiment, the device is used bya driver behind a steering wheel 107, wherein the device is linked to an electronic device or mobile phone 109 via BLUETOOTH connection depicted as 108. As shown in the flow chart of FIG. 2, the proposed eye-tracking system includes a hardware section 201, an algorithm 202 and a mobile application 203 for monitoring and detecting fatigue scale, decision-making capabilities and concentration levels of the user, and in order to take necessary preventive actions. The eye-tracking device (hardware section) 201 and the mobile application 203 are linked via BLUETOOTH technology. The eye-tracking device 201 conducts functions such as acquisition of EOG and EEG signals, transmits and inputs these acquired signals to the algorithm section 202, whose functionalities are to classify the acquired signals and detect a level of fatigue or drowsiness. This classification and detected level (fatigue scale) are then transssmitted to the mobile application 203 in a human readable form, along with necessary preventive measures (or tips) that need to be taken by the user to avoid any mishappenings.

Figure 3:
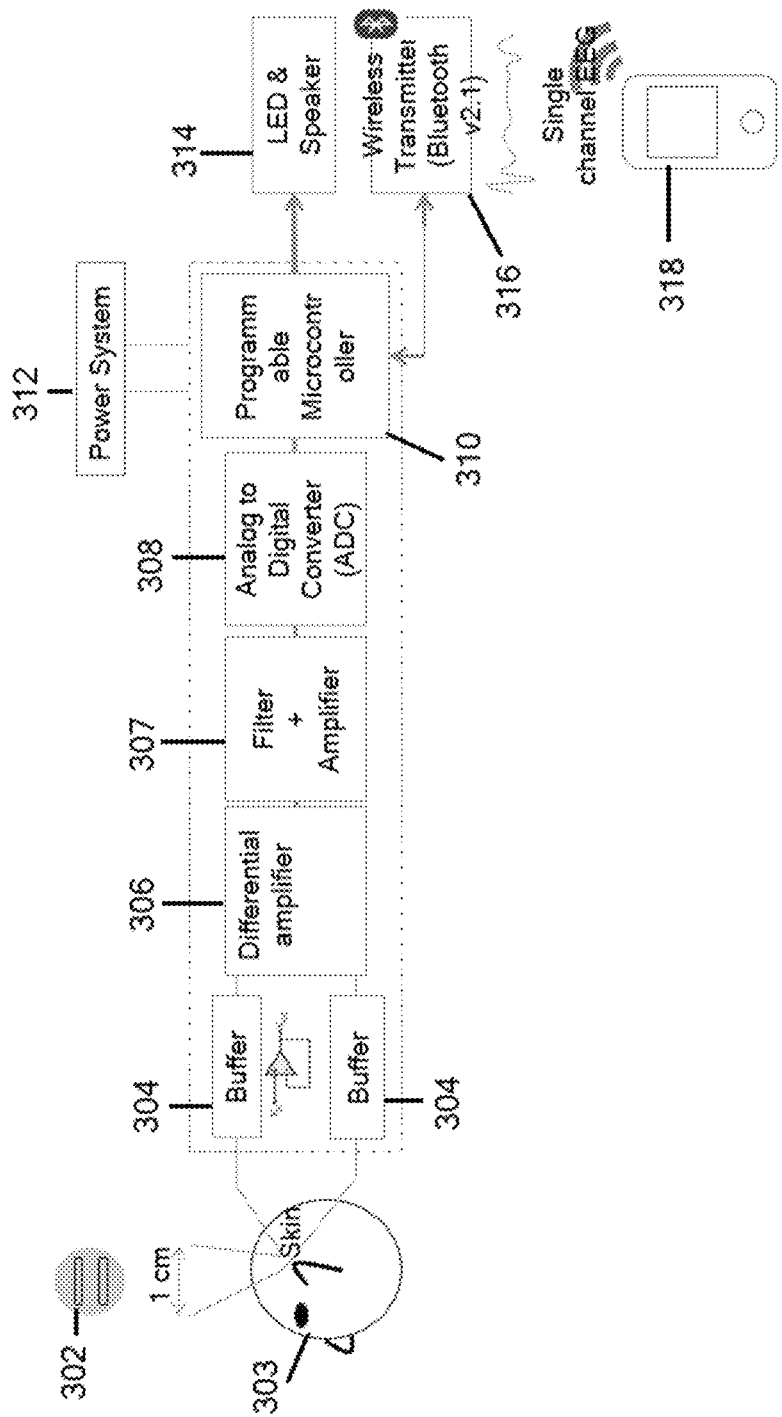
FIG. 3 (a) is a block diagram representing the various electronic components used for recording a user's brain waves and eye movements, and FIG. 3 (b) is the electrical circuit for filter and amplifier used in accordance with the present invention.
Figure 3B:
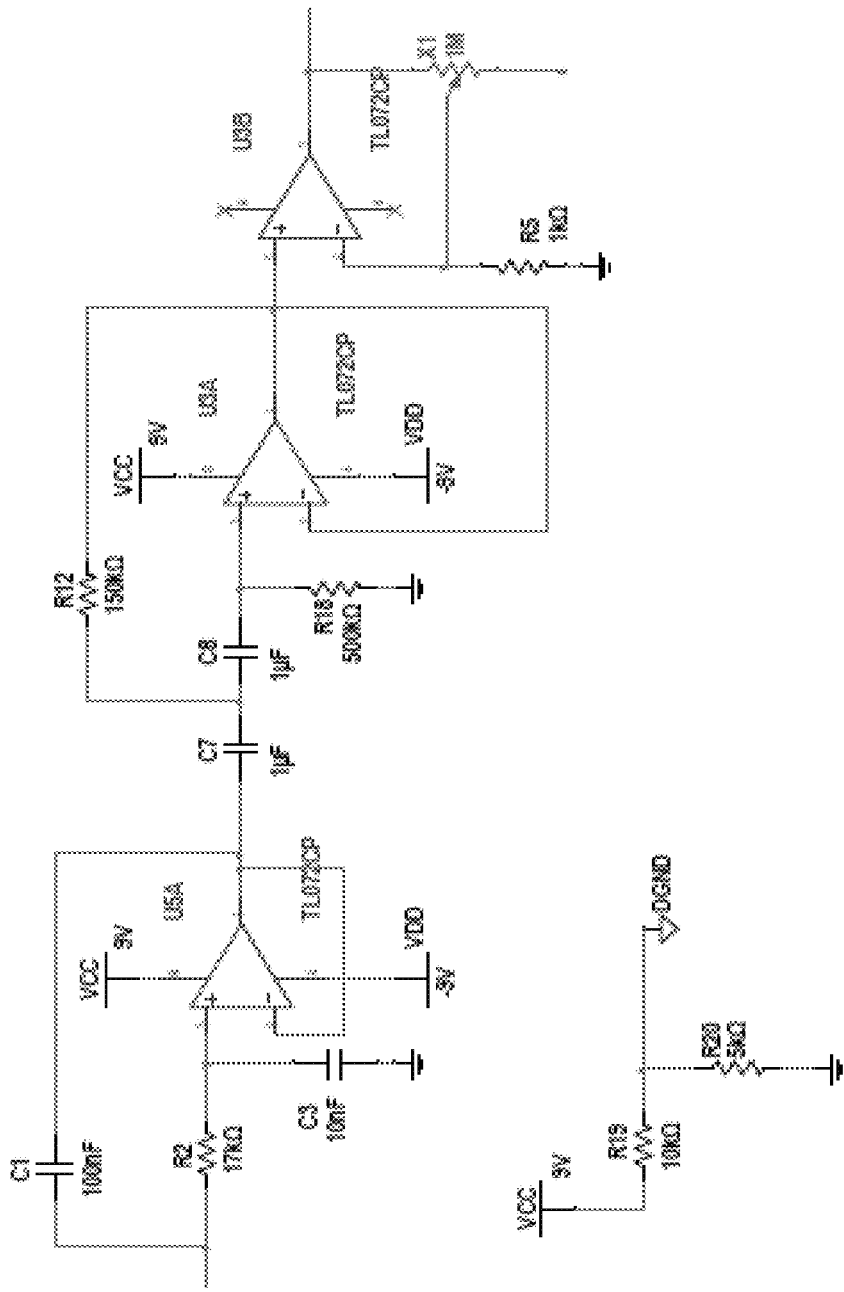
Figure 4:
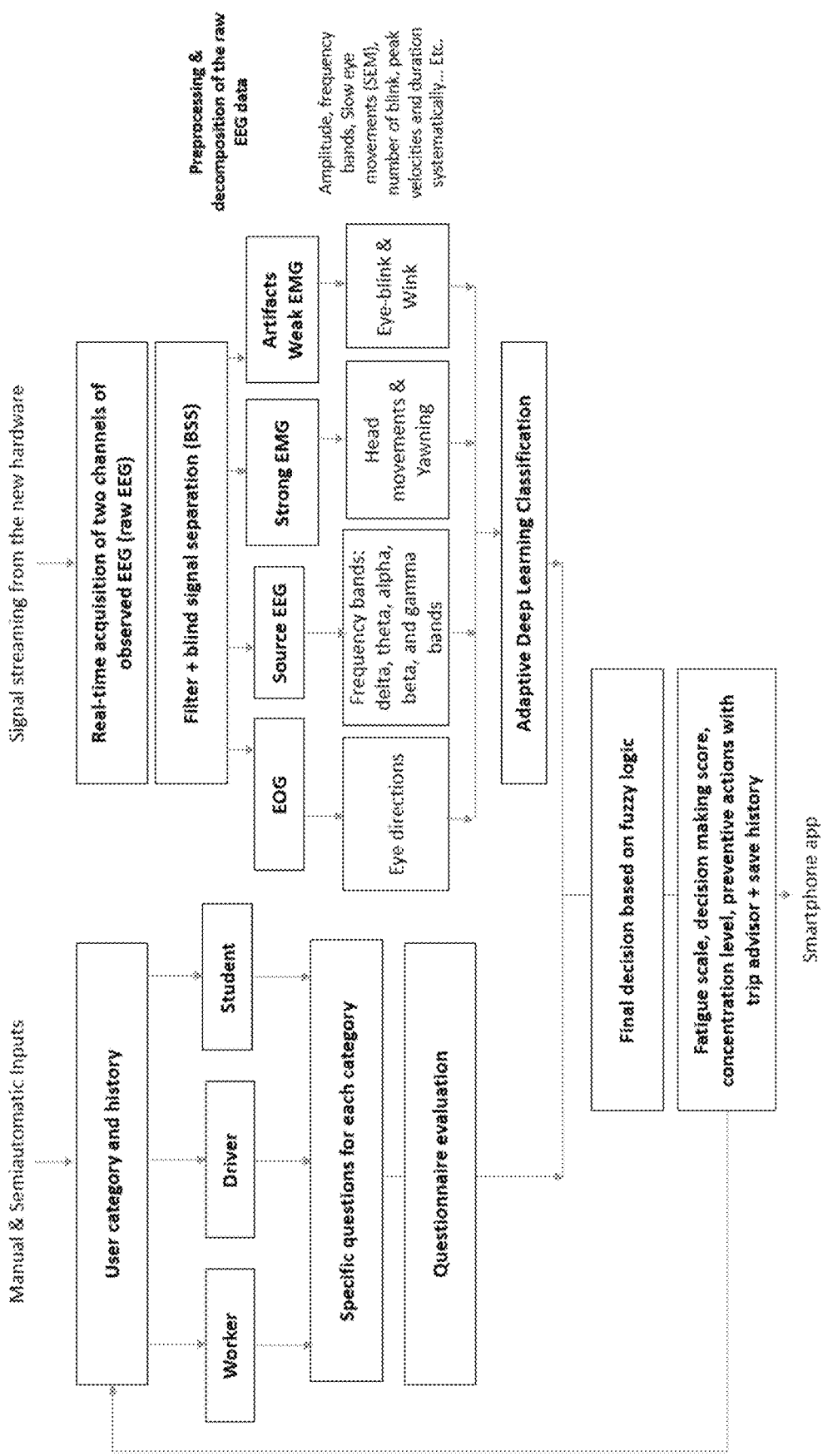
FIG. 4 shows the algorithm flow chart, in accordance with the present invention.

Considering the hardware of the proposed eye-tracking system, FIG. 3 depicts each electronic component used to record brain activity and eye movements (using a low cost device). FIG. 3 (a) is a block diagram representing the various electronic components used for recording a user's brain waves and eye movements, and FIG. 3 (b) is the electrical circuit for filter and amplifier used in accordance with the present invention. The relevant components include a new design for the EEG-EOG electrodes using AgCl 302—each of 1 cm length in contact with the user's skin. The shape of the proposed electrode is very important in order to record a high quality of the EEG signal around the user's ears. Two separate plates or electrodes of AgCl, placed with a spacing of 1 cm between them, are used to play the role of electrical conductors that have an electric potential difference surrounded by an insulator. The surface of each electrode has a rough texture with numerous small solid balls (these balls may be made of gold to achieve high conductivity).

Further components include two buffers 304—for example LMP7708, a differential amplifier 306 for exapmle TL074, filters (including amplifier using a potentiometer) 307—for example TL072CP, an analog to digital converter (ADC) 308—for example MICROCHIP PIC17F876 controller, a microcontroller 310—for example AT90S4433 or ATmega8, or Programmable System-on-Chip (PSoC) CYBL10X6X, a power system 312—such as a small 3V or 9V battery, an LED and speaker 314 and a wireless transmitter (BLUETOOTH v2.1) 316. The filters used in the circuit may be a high-pass filter (0.5 Hz), low-pass filter (30 Hz) along with an amplifier using a potentiometer. The low cost wearable hardware in accordance with the present invention is able to detect eye movements (via EOG signals), blinking patterns, detection of whether eyes are open or closed, temporal EEG signals, yawning patterns and so on.

In another embodiment of the present inevtion, the proposed design has a multi-function capability based on an algorithm for detecting warning signs of fatigue and drowsiness further linked with a mobile application for measuring fatigue scale, monitoring associated decision making capabilities and concentration levels to take preventive actions for its users (which may include, but is not limited to drivers, insurance companies, workers or students). In a preferred embodiment of the present invention, the eye tracking device functions based on an algorithm which deploys feature extraction and analysis, the features comprising amplitudes, peak velocities and durations, frequency bands, etc. Various criteria (neuroscience facts) used for the calibration of the proposed algorithm includes that people blink more when they are tired (the average person blinks 15-20 times per minute), more the person is motivated and active, more his or her signal amplitude will be, slow eye movement (SEM) is an effective indicator for predicting delayed responses to take preventive actions and when a person is driving, his or her eyes must not stop moving for a more than 10 seconds at a time.

The following equation summarizes all signals recorded using the proposed eye-tracking device:

$$EEG(t)_{observed} = EEG(t)_{source} + EOG(t) + EMG(t) + \text{Artifacts}$$

Wherein, $EEG(t)_{observed}$ includes raw electrical signals recorded from around the user's ears, $EEG(t)_{source}$ includes brain activity only to detect frequency bands (alpha or beta), $EOG(t)$ includes detected gaze directions and eye movements related to eyeball, $EMG(t)$ includes head movements and yawning patterns observed and the artifacts include any other minor signs of drowsiness such as excess blinking patterns, etc.

The primary focus is on monitoring and observing brain activity ($EEG_{source}$), user eye movements (EOG) and muscle activity such as yawning frequency, head movements and any other relevant artifacts such as user blinking patterns. The algorithm in accordance with the present invention as depicted as a flow chart in FIG. 4, deals with the classification of warning signs such as fatigue and drowsiness and linking the observations with a mobile application for viewing fatigue scale, decision-making and concentration levels in order to take necessary preventive actions. The algorithm is as follows—INPUT: User's answers of the psychological questions+User history+$EEG_{observed}$ and OUTPUT: Fatigue scale, Decision-making score, Concentration levels, associated and necessary preventive actions Initialize Questionnaire evaluation metric extracted from analyzing the user's answers OR user's history in case user is not a first-time user of the device Decomposing the observed raw signal using filter and blind signal separation method to EOG, brain source signal, and strong and weak EMG signals Feature extraction for building inputs vector from EEG observed: Alpha and Beta frequencies of brain activity (EEG), slow eye movements (SEM), blinking frequency and two channels of eye movements (right and left EOG signals), EMG amplitude, and number of blinks along with its amplitude, etc.

In calibration phase, the classifier (adaptive deep learning) is trained to formulate a model every time a user uses the device, and every model formulated is saved in a small memory.

Loop for each new cycle: Each new input measured is used to test the model-based machine learning.

The model results and questionnaire evaluation results are converted to fatigue scale, decision-making and concentration levels using fussy logic in order to take preventive actions based on a choice of the user.

A final decision is sent as a complete result list (based on the answers of the psychological questions+EEG classification) to a smartphone application to be converted to commands and further to control the LED and speaker.

End for

In another embodiment of the present invention, the eye-tracking device is wirelessly connected to an electronic device, or a mobile application. The proposed smartphone application uses the calculated degree of drowsiness in order to communicate results of the proposed algorithm with the user and provide instructions or alerts to take preventive actions. In another embodiment, the smartphone application allows the user to choose between various profiles such as worker, student or driver, so that the user may obtain a customized set of psychological questions on the basis of the calculated score of drowsiness or concentration and decision making levels. This customizable feature is also to ensure safety of the user and those around him. For example, a worker or laborer who works long shifts in dangerous environments is required to remain active and stay vigilant (thereby also reducing losses borne by insurance companies owing to traffic or work accidents).

In an embodiment, only the results of the classification algorithm, subsequent to applying adaptive learning and fuzzy logic models (which are implemented via a software within the mobile application) are transmitted to the eye-tracking device (the hardware, particularly to the microcontroller, which contains one or more CPUs (processor cores) along with a memory and programmable input/output peripherals). In a situation where there is a break of communication between the smartphone and the proposed eye-tracking device—the processing is done within the hardware itself (it works like a backup). However, in normal cases, in order to preserve battery power, all the processing is done by the mobile application.

The following table explains a sample case of calculating the degree of drowsiness of a user. In addition, the degree of user drowsiness or fatigue is proportional to concentration and decision-making levels. Concentration level is proportional to Beta band power since Beta band is associated with focused concentration and best defined in central and frontal brain areas. However, thinking of something peaceful with eyes closed results in an increase of alpha activity.

| USER PROFILES | | | | | |
|---|---|---|---|---|---|
| Degree of Drowsiness | Scale rating | Preventive Action or Feedback | Driver Fatigue scale | Student Concentration scale | Worker Decision-making scale |
| Functioning at peak | 10% | Green light | Best time to pick your destination | Best time to study and practice | Best time to make an important decision |
| Functioning at high level, but not at peak; Able to concentrate | 20% | Green light | Best time to pick your destination | Best time to study and practice | Best time to make an important decision |
| Feeling active, vital and alert | 30% | Green light | Best time to pick your destination | Best time to study and practice | Best time to make an important decision |
| Awake, but relaxed; Responsive but not fully alert - Level 1 | 40% | Orange light + Coffee break | Best time to pick your destination | Best time to study and practice | Best time to make an important decision |
| Awake, but relaxed; Responsive but not fully alert - Level 2 | 50% | Red light + 1 beep + tips | You can still drive but be carful | You can still study if you have exams but it might be better to take some rest | It is not recommended to take important decisions |
| Somewhat foggy; slowing down | 60% | Red light + 5 beeps + tips | You can still drive but be carful | You can still study if you have exams but it might be better to take some rest | It is not recommended to take important decisions |
| Fighting drowsiness - Level 1 | 70% | 5 beeps + strong vibration | It might be better to stop driving | You can still study if you have exams but it might be better to take some rest | It is not recommended to take important decisions |
| Fighting drowsiness - Level 2 | 80% | 10 beeps + strong vibration | Stop driving, your life is in dangerous | You are wasting your time. Your brain needs some rest | Don't take an important decision |

-continued

USER PROFILES

| Degree of Drowsiness | Scale rating | Preventive Action or Feedback | Driver Fatigue scale | Student Concentration scale | Worker Decision-making scale |
|---|---|---|---|---|---|
| Foggy and losing interest in staying awake; slow down | 90% | 10 beeps + 5 strong vibrations | Stop driving, your life is in dangerous | You are wasting your time. Your brain needs some rest | Don't take an important decision |
| Closed eyes, drowsing, Fighting sleep Asleep with open eyes, looking but not seeing | 100% | Red light + Non-stop strong beeps and vibrations | Stop driving, your life is in dangerous | You are wasting your time. Your brain needs some rest | Don't take an important decision |

The displayed contents or results are based on the answers input by the user for the psychological questions along with using a classification algorithm on the observed or recorded EEG signals. In another embodiment of the present invention, a classification algorithm is developed and used for distinguishing between brain activity (using Alpha and Beta frequency bands for sleeping time and awake time, concentration intensity and decision making capabilities) and eye movements (based on detection of blinking patterns and gaze directions). The proposed algorithm (which is based on answers to the psychilogical questions and the detected EEG signals) converts the signals obtained from the user into a a degree of drowsiness, wherein Alpha bands appears when the user is drowsy or relaxed and Beta bands appears when the user is awake or active.

In another preferred embosiment of the present invention, the proposed eye-tracking device is linked with a mobile application installed on an electronic device. The feature which differentiates the proposed design from traditionally used devices is that the proposed eye-tracking device is compact and suitable for simply fixing around the user's ears, as a result of which no obstructions are created to the field of vision of the user. Further, the proposed device is a low-cost hardware. This invention is maily intended to solve drowsy driving issues and to prevent drivers from falling asleep momentarily, and thereby to avoid car accidents using an affordable or low-cost device. The proposed device also is able to check fatigue and concentration levels of workers or students to improve their decision-making capabilities.

The proposed eye-tracking system monitors and records features such as brain activity or brain waves, eye movements, winking and blinking patterns, head movements and also history data of the user (combination of physiological signals and user's answers from a questionnaire). Each user possesses different fatigue scales using the same algorithm. For example, if the user is a student, the mobile phone application presents a scale of fatigue or concentration along with some advice for students. If the user is a driver, the application presents fatigue scale with some advice for drivers. In addition, if the user is a shift worker, the application will present fatigue or decision-making scale along with additional advice related to shift workers. The proposed algorithm uses only two EEG electrodes around the user's ear to record numerous relevant signals that are classified into patterns to be used for deep learning method. Subsequently, the combination of the results from deep learning and the questionnaire evaluation results are used as input for fussy logic classifier to output to the user a percentage of his or her fatigue.

This proposed design of a low-cost wearable eye tracking device is further aesthetically suitable for both men and women. Even a woman who wears a veil (Hijab) or a man who wears traditional clothes can utilize this good looking device hidden around their ears (preferably two similar devices around each ear to have accurate results). The device is beneficial for drivers, insurance companies, workers, and students to improve their daily-life performances, and is useful in various fields and suitable for daily life applications. One of its important applications is for detecting the warning signs of fatigued and drowsy driving with mobile phone application. The users are not required to physically look at the electronic device during use, since the mobile application provides the user with timely auditory, visual and haptic warnings or alert messages.

Many changes, modifications, variations and other uses and applications of the subject invention will become apparent to those skilled in the art after considering this specification and the accompanying drawings, which disclose the preferred embodiments thereof. All such changes, modifications, variations and other uses and applications, which do not depart from the spirit and scope of the invention, are deemed to be covered by the invention, which is to be limited only by the claims which follow.

The invention claimed is:

1. A method of preventing drowsy driving, low concentration and bad decision making of a user using an eye-tracking device positioned around the user's ears, the method comprising the steps of:
   obtaining a temporal EEG (electro-encephalogram) signal using two EEG electrodes, separated by 1 cm and configured to be in contact with the user's ear, wherein a surface of each electrode comprises a plurality of solid gold balls for increasing conductivity of the two EEG electrodes;
   processing the obtained temporal EEG signal to generate information, classifying the information using an adaptive deep learning classifier;
   applying a fuzzy logic classifier to a combination of the classified information and the user's inputs from a plurality of psychological questions to obtain final results, wherein the final results comprise a calculated fatigue scale, decision-making score and concentration level; and
   determining a condition of the user from the final results and sending a customized visual or audio notification signal to the user depending on particular user profiles including workers, drivers and students, wherein the customized visual or audio notification comprises instructions including instructions for stopping a vehicle, washing face, having a coffee or for taking a power nap.

2. The method of claim 1, wherein processing the obtained temporal EEG signal comprises:
decomposing the obtained EEG signal using filter and blind signal separation techniques into a plurality of features.

3. The method of claim 2, wherein the plurality of psychological questions are customized based on a profile of the user, thereby enabling the customized visual or audio notification signal to be provided to the user depending on the determined condition of the user.

4. The method of claim 2, wherein the features are the generated information, and they are subsequently combined with a calculated evaluation metric based on the user's inputs as input to the fuzzy logic classifier.

5. The method of claim 2, wherein an output of the fuzzy logic classifier is a percentage of the user's fatigue level.

6. The method of claim 1, wherein the condition of the user is a fatigue level, a drowsiness level, or a physiological status.

7. The method of claim 1, wherein the obtained EEG signal comprises left and right electro-oculography (EOG) signals.

8. The method of claim 1, wherein the processing of the EEG signal comprises decomposing the EEG signal into features comprising alpha and beta frequency bands, slow eye movements, blinking amplitudes and patterns and eletromyography (EMG) amplitudes.

9. The method of claim 1, wherein the eye-tracking device is operatively connected with a mobile application installed on a mobile device, and wherein the processing of the EEG signal is conducted using a mobile application running on the mobile device.

10. The method of claim 1, wherein the electrodes are selected from the group of silver chloride (AgCl) electrodes and AgCl electrode plates.

11. The method of claim 1, wherein the user is able to view the final results through a mobile application.

12. A wearable eye-tracking device for preventing drowsy driving, low concentration and bad decision making of a user, the eye-tracking device comprising:
two EEG (electro-encephalogram) electrodes separated by 1 cm and configured to be in contact with the user's ear for obtaining a temporal EEG signal from the user,
a microprocessor for processing the obtained temporal EEG signal to generate information, classifying the information using an adaptive deep learning classifier, and determining a condition of the user by applying a fuzzy logic classifier to the classified information in combination with the user's inputs for a plurality of psychological questions to obtain final results, wherein the finals results comprise a calculated fatigue scale, decision-making score and concentration level, and
a communication unit in electrical communication with the microprocessor for sending a customized visual or audio notification signal to the user depending on particular user profiles including workers, drivers and students, wherein the customized visual or audio notification comprises instructions including instructions for stopping a vehicle, washing face, having a coffee or for taking a power nap, and
wherein a surface of each electrode comprises a plurality of solid gold balls for increasing conductivity of the two EEG electrodes of the eye-tracking device.

13. The wearable eye-tracking device of claim 12, wherein processing the EEG signal comprises processing two channels of eye movements or left and right electro-oculography (EOG) signals.

14. The wearable eye-tracking device of claim 13, wherein processing the EEG signal comprises:
decomposing the obtained EEG signal using filter and blind signal separation techniques into a plurality of features.

15. The wearable eye-tracking device of claim 12 wherein the communication unit comprises a Bluetooth communication system and at least one of a tri-colored LED indicator, a speaker and a vibrator.

16. The wearable eye-tracking device of claim 12, wherein the two electrodes are selected from the group of AgCl electrodes and AgCl electrode plates.

17. The wearable eye-tracking device of claim 12, wherein the device is adapted to be worn by the user such that it is positioned away from a visual field of the user, and wherein the device further comprises a support for enabling the device to be fixed around the user's ear during operation.

18. The wearable eye-tracking device of claim 12, wherein the processing of the EEG signal comprises decomposing the EEG signal into features comprising alpha and beta frequency bands, slow eye movements, blinking amplitudes and pattern and electromyography (EMG) amplitudes.

19. The wearable eye-tracking device of claim 12, wherein the user is able to view the final results through a mobile application.

* * * * *